United States Patent
Vedel et al.

(10) Patent No.: US 12,150,968 B2
(45) Date of Patent: Nov. 26, 2024

(54) METHOD FOR REDUCING THE TRANSFER OF PATHOGENIC MICROORGANISMS

(71) Applicant: Lactobio A/S, Copenhagen (DK)

(72) Inventors: Charlotte Vedel, Copenhagen (DK); Ida Blomquist Jørgensen, Copenhagen (DK); Søren Kjærulff, Copenhagen (DK)

(73) Assignee: L'Oreal S.A., Paris (FR)

( * ) Notice: Subject to any disclaimer, the term of this patent is extended or adjusted under 35 U.S.C. 154(b) by 15 days.

(21) Appl. No.: 17/272,640

(22) PCT Filed: Aug. 8, 2019

(86) PCT No.: PCT/EP2019/071343
§ 371 (c)(1),
(2) Date: Mar. 1, 2021

(87) PCT Pub. No.: WO2020/052869
PCT Pub. Date: Mar. 19, 2020

(65) Prior Publication Data
US 2022/0000948 A1    Jan. 6, 2022

(30) Foreign Application Priority Data

Sep. 10, 2018 (DK) ............................ PA 2018 00557
Apr. 17, 2019 (DK) ............................ PA 2019 00468

(51) Int. Cl.
*A61K 35/747* (2015.01)
*A61K 35/744* (2015.01)
*A61P 31/04* (2006.01)

(52) U.S. Cl.
CPC .......... *A61K 35/747* (2013.01); *A61K 35/744* (2013.01); *A61P 31/04* (2018.01)

(58) Field of Classification Search
CPC ...... A61K 35/747; A61K 35/744; A61P 31/04
See application file for complete search history.

(56) References Cited

U.S. PATENT DOCUMENTS

| | | | |
|---|---|---|---|
| 3,897,307 A * | 7/1975 | Porubcan | A23C 9/1234 435/253.4 |
| 5,032,399 A | 7/1991 | Gorbach et al. | |
| 5,171,591 A | 12/1992 | Whiting | |
| 5,242,593 A | 9/1993 | Oberkofler et al. | |
| 5,360,517 A | 11/1994 | Guerineau et al. | |
| 5,863,882 A | 1/1999 | Lin et al. | |
| 6,051,552 A * | 4/2000 | Reid | C12P 1/04 424/234.1 |
| 2004/0022775 A1 | 2/2004 | Reid et al. | |
| 2006/0067923 A1 | 3/2006 | Ushida et al. | |
| 2009/0304656 A1 | 12/2009 | Roos | |
| 2014/0308258 A1 | 10/2014 | Matthews et al. | |
| 2017/0224750 A1 | 8/2017 | Callanan et al. | |

FOREIGN PATENT DOCUMENTS

| | | |
|---|---|---|
| AU | 719544 B2 | 5/2000 |
| CN | 102698310 A | 10/2012 |
| CN | 103596452 A | 2/2014 |
| CN | 106573023 A | 4/2017 |
| DE | 202017105515 U1 | 8/2018 |
| EP | 2823822 A1 | 1/2015 |
| FI | 92498 B | 8/1994 |
| JP | 3417904 B2 | 6/2003 |
| KR | 20120038698 A | 4/2012 |
| KR | 101258692 B1 | 4/2013 |
| KR | 101739122 B1 | 5/2017 |
| WO | 2005/079210 A2 | 9/2005 |
| WO | WO-2006/031554 A2 | 3/2006 |
| WO | 2010/056198 A1 | 5/2010 |
| WO | 2012/156491 A1 | 11/2012 |
| WO | WO-12152270 A1 | 11/2012 |
| WO | 2016/023688 A1 | 2/2016 |
| WO | WO 2017/084985 A1 | 5/2017 |
| WO | WO-2017173242 A1 * | 10/2017 ............. A61K 35/74 |

OTHER PUBLICATIONS

Crouzet, et al., "Lactobacillus Paracasei CNCM I-3689 Reduces Vancomycin-Resistant Enterococcus Persistence And Promotes Bacteroidetes Resilience In The Gut Following Antibiotic Challenge," *Scientific Reports*, 8(5098): 1-11 (2018).
Brachkova, et al., "Preservation Of Viability And Antibacterial Activity Of *Lactobacillus* Spp. In Calcium Alginate Beads," *European Journal Of Pharmaceutical Sciences*, 41: 589-596 (2010).
Bendjeddou, et al., "Characterization And Purification Of A Bacteriocin From *Lactobacillus paracasei* Subsp. Paracasei BMK2005, An Intestinal Isolate Active Against Multidrug-Resistant Pathogens," *World Journal Of Microbiology And Biotechnology*, 28: 1543-1552 (2012).
Search Report from Danish Application No. PA 2018 00557, dated: Mar. 11, 2019.
International Search Report from PCT/EP2019/071343, dated Nov. 21, 2019.
Wertheim, et al., "The Role of Nasal Carriage in *Staphylococcus aureus* Infections," *Lancet Infect. Dis.*, 5(12): 751-762 (2005).
Barrett, et al., "Methicillin-Resistant *Staphylococcus aureus* at Boston City Hospital, Bacterial and Epidemiologic Observations," *New England J Med.* 279: 441-448 (1968).
Jevons, " "Celbenin"-resistant *Staphylococci,*" *British Med. J.* 1(5219):124-125 (1961).
<https://www.cdc.gov/mrsa/tracking/index.html>.
Dantes, et al., "National Burden of Invasive Methicillin-Resistant *Staphylococcus aureus* Infections, United States, 2011," *JAMA Int. Med.* 173(21): 1970-1978 (2013).

(Continued)

*Primary Examiner* — Jana A Hines
*Assistant Examiner* — Khatol S Shahnan Shah
(74) *Attorney, Agent, or Firm* — Honigman LLP

(57) ABSTRACT

The present invention relates to a composition comprising at least one lactic acid bacterium for use in decreasing the transfer of a pathogenic microorganism between a surface of a first subject and a surface of a second subject.

40 Claims, No Drawings

(56) References Cited

OTHER PUBLICATIONS

Defres et al., "MRSA as a Cause of Lung Infection Including Airway Infection, Community Acquired Pneumonia and Hospital-Acquired Pneumonia," *Eur. Resp. J.* 34(6): 1470-1476 (2009).
García-Álvarez, et al., "Meticillin-resistant *Staphylococcus aureus* with a Novel mecA Homologue in Human and Bovine Populations in the UK and Denmark: A Descriptive Study," *Lancet Infect. Dis.* 11(8): 595-603 (2011).
Shore, et al., "Detection of Staphylococcal Cassette Chromosome mec Type XI Carrying Highly Divergent mecA, mecI, mecR1, blaZ, and ccr Genes in Human Clinical Isolates of Clonal Complex 130 Methicillin-Resistant *Staphylococcus aureus*," *Antimicrob. Agents Chemo.* 55(8): 3765-3773 (2011).
De Boer, et al., "Prevalence of Methicillin-Resistant *Staphylococcus aureus* in Meat," *Int. J. Food Microbiol.* 134(1-2): 52-56 (2009).
NIAID, <https://www.niaid.nih.gov/research/mrsa-methicillin-resistant-staphylococcus-aureus>.
Köck, et al., "Methicillin-resistant *Staphylococcus aureus* (MRSA): Burden of Disease and Control Challenges in Europe," *Eurosurveillance* 15(41): 19688 (2010).
Shigemura, et al., "Pathogen Occurrence and Antimicrobial Susceptibility of Urinary Tract Infection Cases During a 20-Year Period (1983-2002) at a Single Institution in Japan," *Japan. J. Infect. Dis.* 58(5): 303-308 (2005).
Conway, et al., "Survival of Lactic Acid Bacteria in the Human Stomach and Adhesion to Intestinal Cells," *J. Dairy Sci.* 70:1-12 (1987).
Goldin, et al., "Survival of *Lactobacillus* Species (Strain GG) in Human Gastrointestinal Tract," *Dig. Dis. Sci.* 37:121-128 (1992).
Kleeman and Klaenhammer, "Adherence of *Lactobacillus* Species to Human Fetal Intestinal Cells," *J. Dairy Sci.* 65:2063-2069 (1982).
Castagliuolo, et al., "*Saccharomyces boulardii* Protease Inhibits *Clostridium difficile* Toxin A Effects in the Rat Ileum," *Infect. Immun.* 64:5225-5232 (1996).
Castagliuolo, et al., "*Saccharomyces boulardii* Protease Inhibits the Effects of *Clostridium difficile* Toxins A and B in Human Colonic Mucosa," *Infect. Immun.* 67:302-307 (1999).
Pothoulakis, et al., "*Saccharomyces boulardii* Inhibits *Clostridium difficile* Toxin A Binding and Enterotoxicity in Rat Ileum," *Gastroenterology* 104:1108-1115) (1993).
Fukushima, et al., "Effect of a Probiotic Formula on Intestinal Immunoglobulin A Production in Healthy Children," *Int. J. Food Microbiol.* 42:39-44 (1998).
Malin, et al., "Promotion of IgA Immune Response in Patients with Crohn's Disease by Oral Bacteriotherapy with *Lactobacillus* GG," *Ann. Nutr. Metab.* 40:137-145 (1996).
Dowarah, et al. "Selection and Characterization of Probiotic Lactic Acid Bacteria and its Impact on Growth, Nutrient Digestibility, Health and Antioxidant Status in Weaned Piglets," *PLoS ONE*, 13(3) (2018).
Khare and Tavazoie, "Multifactorial Competition and Resistance in a Two-Species Bacterial System," *PLoS Genetics*, 11(12), 1-21 (2015).
Office Action issued on Sep. 16, 2023 in CN Application No. 201980059563.9.
English Translation of Office Action issued on Sep. 16, 2023 in CN Application No. 201980059563.9.

\* cited by examiner

METHOD FOR REDUCING THE TRANSFER OF PATHOGENIC MICROORGANISMS

RELATED APPLICATIONS

This application is a national stage filing under 35 U.S.C. 371 of International Application No. PCT/EP2019/071343, filed Aug. 8, 2019, which claims priority to Denmark Application No. PA 2018 00557, filed Sep. 10, 2018, and Denmark Application No. PA 2019 00468, filed Apr. 17, 2019. The entire teachings of said applications are incorporated by reference herein.

TECHNICAL FIELD OF THE INVENTION

The present invention relates to a method of transferring pathogenic microorganisms. In particular, the present invention relates to the transfer of pathogenic microorganisms between a surface of a first subject and a surface of a second surface.

BACKGROUND OF THE INVENTION

Pathogen microorganisms are microorganism that may cause the development of a disease in a mammal and may embrace bacterial microorganisms; viral microorganisms; fungal microorganisms; parasite microorganisms; and algal microorganisms. The Gram-positive bacterium, *Staphylococcus aureus*, is one of the most frequently encountered human pathogens.

With the discovery of penicillin in 1928, and its mass production in the early 1940s, infections with *S. aureus* were mostly treatable, without any major complications. However, clinicians soon observed the emergence of penicillin-resistant strains of *S. aureus*, which was largely due to bacterial expression of beta-lactamases, enzymes that disrupt the beta-lactam ring structure in the penicillin and cephalosporin classes of antibiotics (beta-lactam antibiotics), destroying their antimicrobial activity. Methicillin, a novel penicillin analogue that was resistant to beta-lactamases, was introduced in 1959, and was initially effective against penicillin-resistant *S. aureus* strains. However, this success was short-lived, as the first methicillin-resistant *S. aureus* (MRSA) strain had been identified in the laboratory by 1961, and cases of MRSA were first observed in the clinic in 1968.

Initially, MRSA strains only occurred in small and local outbreaks across the US and Europe, but they can now be found around the world. Today, approximately 2% of the US population is thought to carry a MRSA strain.

MRSA infections was predominantly occurring in the hospital settings and is a leading cause of a variety of hospital-acquired infections (HAIs). Since the 1990s, a new type of MRSA, known as community-associated MRSA (CA-MRSA), has emerged. CA-MRSA can not only be distinguished genetically from healthcare-associated MRSA (HA-MRSA) strains, but also exhibits different virulence and antibiotic resistance patterns.

Recently, crossing of different CA-MRSA and HA-MRSA strains has been observed, which often makes it difficult to determine the origin of the infecting MRSA strain.

The overall prevalence of MRSA infections in the US is currently below 100,000 cases, resulting in about 11,000 deaths annually. With the development of new antibiotics against MRSA and other bacterial infections, *S. aureus* has acquired and developed new resistance pathways, as highlighted by the emergence of *S. aureus* strains resistant to oxacillin, clindamycin, trimethoprim-sulfamethoxazole, and Zyvox (linezolid), which has led to MRSA strains that are resistant to multiple classes of antibiotics.

A final line of defense in the treatment of invasive MRSA infections has been the glycopeptide antibiotic, vancomycin. However, MRSA strains with either highly limited susceptibility to vancomycin, known as vancomycin-intermediate *S. aureus* (VISA), or resistance to vancomycin, known as vancomycin-resistant *S. aureus* (VRSA), have emerged worldwide.

Treatment of infections resulting from pathogenic microorganisms, such as MRSA infections may be subjected to different modes of action. One mode of action relates to the direct treatment of an infected subject, e.g. the antibiotic treatment of MRSA infected human or animal (livestock), as mentioned above. Another mode of action, different from treating the pathogenic microorganism when infected, is prevention of infection by pathogenic microorganisms, by reducing the transfer of the pathogenic microorganisms from one subject to another.

MRSA may be spread in different ways:
  Skin-to-skin contact. MRSA can be transmitted from one person to another by skin-to-skin contact. While MRSA skin infections can occur in participants of many types of sports, they're much more likely to occur in contact sports—such as football, wrestling and rugby.
  Touching contaminated objects. If drainage from an MRSA skin infection comes into contact with an object—like a towel, handles, weight training equipment or a shared jar of ointment—the next person who touches that object may become infected with MRSA bacteria.

In order to avoid such spread of MRSA, towels, handles, wrestling mats, weight training equipment, locker room benches athletic equipment and locker rooms, etc. should be regularly cleaned and disinfected.

Thus, there are many ways in which one may be infected by pathogenic microorganisms and a first line of defence may be to reduce transfer of the pathogenic microorganisms between surfaces or subjects and the second line of defence may be treatment of the pathogenic microorganism when infected.

Hence, alternative modes of action when fighting against the spread and infection of pathogenic microorganisms would be advantageous, and in particular a more efficient and/or reliable composition suitable for reducing or even avoiding transfer of pathogenic microorganisms between a surface of a first subject and a surface of a second surface would be advantageous.

SUMMARY OF THE INVENTION

Thus, an object of the present invention relates to a method of reducing the transfer of pathogenic microorganisms between surfaces.

In particular, it is an object of the present invention to provide a composition and a method that solves the above mentioned problems of the prior art with transferring of pathogenic microorganisms, like MRSA.

Thus, one aspect of the invention relates to a composition comprising at least one lactic acid bacterium for use in decreasing the transfer of a pathogenic microorganism between a surface of a first subject and a surface of a second subject.

Another aspect of the present invention relates to a method for reducing transfer of a pathogenic microorganism between a surface of a first subject and a surface of a second subject by administrating a composition having an effective amount of at least one lactic acid bacterium.

Yet another aspect of the present invention relates to the use of a composition according to the present invention for reducing the transfer of an antibiotic resistant microorganism between a surface of a first subject and a surface of a second subject.

DETAILED DESCRIPTION OF THE INVENTION

Despite improvements in the treatment of pathogenic microorganisms, such as invasive MRSA infections, especially those with an onset in the community or livestock setting, such treatment remains problematic and result in a significant financial burden for the healthcare systems. Since pathogenic infections, like MRSA, are spread through direct contact with another infected person, such as by sharing personal items that have touched infected skin, or by touching contaminated subjects including skin, nasal passages, animals, surfaces or similar items, the present inventors found an alternative way to avoid infections by pathogenic microorganisms, like MRSA.

Hence, the present invention provides a new method and a new composition for reducing the transfer of MRSA between subjects. Thus, the present invention provides a mode of avoiding infection by pathogenic microorganisms, like MRSA infections.

Thus, one aspect according to the present invention relates to a composition comprising at least one lactic acid bacterium for use in decreasing the transfer of a pathogenic microorganism between a surface of a first subject and a surface of a second subject.

In an embodiment of the present invention, the first subject may be a first mammal or a first fabric material.

In a further embodiment of the present invention, the second subject may be selected from a second mammal, a hard surface selected from a metal material; a steel material; a wood material; a plastic material; a rubber material; a glass material; a second fabric material and/or a silicone material.

The first mammal and the second mammal is preferably not the same mammal.

In an embodiment of the present invention the transfer of a pathogenic microorganism may be decreased at least 10%; such as at least 20%, e.g. at least 30%; such as at least 40%, e.g. at least 50%; such as at least 60%, e.g. at least 70%; such as at least 80%, e.g. at least 90%; such as full blockage.

This decrease is determined relative to the transfer of pathogenic microorganisms observed when not using the composition according to the present invention. The number of microorganisms on a subject may be measured as Colony Forming Units CFU/cm2.

In yet an embodiment of the present invention the pathogenic microorganism may be a microorganism resistant to antibiotics.

In a further embodiment of the present invention the microorganism resistant to antibiotics may be a bacterium resistant to antibiotics.

Preferably the bacterium resistant to antibiotics may be Methicillin resistant *Staphylococcus* and/or a Vancomycin resistant *Enterococcus* species.

Pathogenic microorganisms, such as *S. aureus*, not only infects humans, but also other mammals, infected livestock have been an additional origin of transmission. Livestock-associated MRSA (LA-MRSA) has been identified, mostly in pig populations, with colonization rates varying drastically, from 10-80%, but is also found in ruminants and poultry.

Subjects like stables, stalls, animals, farmers, farmers household members, personal and visitors of stables as well as slaughter houses and animal transport vehicles get contaminated with LA-MRSA. These subjects can carry the LA-MRSA and be the reason for the LA-MRSA to be transferred between subjects and thus spreading the LA-MRSA in stables, among livestock as well as in livestock associated community and further into community resulting in an increased risk of MRSA being spread among healthy carriers, also with a further risk of spreading the MRSA through carriers into hospitals or nursery homes. Today there is no solution to limit or reduce this risk. More and more stables and livestock get contaminated and MRSA transfers between carrier subjects. The present invention relates to a method to reduce this transfer of MRSA between carriers. The present invention also relates to a composition and to new microbial strains which can reduce the transfer of MRSA between carriers.

In some cases, patients suffer from recurring MRSA infections. However, MRSA infection does not develop into a chronic disease; rather, the patients was either never completely cleared of the MRSA strain, which can take several months, or was re-introduced to it. Such re-introduction can result from exposure to the same source that originally introduced the MRSA strain to the patient, such as a colonized household member, medical device, pet, livestock, stall or livestock facilities.

MRSA can be categorized according to the setting in which the infection was acquired as either HA-MRSA or CA-MRSA or LA-MRSA. HA-MRSA is acquired in the hospital or nursing home, and has increased in the US during the past decade due to a number of factors, including an increased number of immunocompromised and elderly patients, an increase in the number of invasive procedures, and failures in infection control measures, such as hand washing prior to patient contact and the removal of non-essential catheters. A dramatically increase in LA-MRSA has also been reported and this has in some countries outnumbered the incidence of HA-MRSA.

Preferably the surface of the first mammal and/or the surface of the second mammal may be the skin; the hair; the nails; and/or the hoofs.

The present invention relates to a composition which can reduce or inhibit transfer of pathogenic microorganisms, such as MRSA. In particular, the composition according to the present invention may be used for prevention of MRSA infections to be transferred from one subject to another subject and/or for reducing the level of HA-MRSA and/or CA-MRSA and/or LA-MRSA.

The at least one lactic acid bacterium according to the present invention may preferably be selected from the genera *Lactobacillus, Leuconostoc, Bifidobacterium, Pediococcus, Lactococcus, Streptococcus Aerococcus, Carnobacterium, Enterococcus, Oenococcus, Sporolactobacillus, Tetragenococcus, Vagococcus*, and *Weissella. Lactobacillus* may be preferred.

In an embodiment of the present invention the preferred at least one lactic acid bacteria may be selected from the group comprising *Lactobacillus lactis, Lactobacillus rhamnosus, Lactobacillus casei, Lactobacillus plantarum, Lactobacillus brevis, Lactobacillus helveticus, Lactobacillus reuteri, Lactobacillus jensenii, Lactobacillus acidophilus, Lactobacillus bulgaricus, Lactobacillus amylovorus, Lacto-*

*bacillus delbrueckii, Lactobacillus crispatus, Lactobacillus gasseri, Lactobacillus johnsonii, Lactobacillus paracasei, Lactobacillus pentosus, Lactobacillus curvatus, Lactobacillus buchneri, Lactobacillus fructivorans, Lactobacillus hilgardii, Lactobacillus fermentum, Lactobacillus viridescens, Bifidobacterium bifidum, Lactobacillus ingluviei* or analogs, derivatives, or fragments thereof;

In a preferred embodiment of the present invention the at least one lactic acid bacteria have a genetic homology of at least 95% to one or more of the bacterial strains selected from the group consisting of:

*Weissella viridescens* LB10G, which is deposited as DSM 32906;
*Lactobacillus paracasei* LB113R, which is deposited as DSM 32907;
*Lactobacillus plantarum* LB244R, which is deposited as DSM 32996;
*Lactobacillus paracasei* LB116R, which is deposited as DSM 32908;
*Enterococcus faecium* LB276R, which is deposited as DSM 32997;
*Lactobacillus plantarum* LB316R, which is deposited as DSM 33091;
*Leuconostoc mesenteriodes* LB341R
*Leuconostoc mesenteriodes* LB349R, which is deposited as DSM 33093;
*Lactobacillus plantarum* LB356R, which is deposited as DSM 33094;
*Lactobacillus plantarum* LB312R, which is deposited as DSM 33098;

In a further preferred embodiment of the present invention the at least one lactic acid bacteria have a genetic homology of at least 95% to one or more of the bacterial strains selected from the group consisting of:

*Weissella viridescens* LB10G, which is deposited as DSM 32906;
*Lactobacillus paracasei* LB113R, which is deposited as DSM 32907;
*Lactobacillus plantarum* LB244R, which is deposited as DSM 32996;
*Lactobacillus paracasei* LB116R, which is deposited as DSM 32908;
*Enterococcus faecium* LB276R, which is deposited as DSM 32997;
*Lactobacillus plantarum* LB316R, which is deposited as DSM 33091;
*Leuconostoc mesenteriodes* LB349R, which is deposited as DSM 33093;
*Lactobacillus plantarum* LB356R, which is deposited as DSM 33094;
*Lactobacillus plantarum* LB312R, which is deposited as DSM 33098;

In an even further preferred embodiment of the present invention the genetic homology may be at least 96%; such as at least 97%; e.g. at least 98%; such as at least 99%; e.g. at least 99.5%; such as at least 99.8%; e.g. at least 99.9%; such as 100% (identical) to one or more of the bacterial strains selected from the group consisting of:

*Weissella viridescens* LB10G, which is deposited as DSM 32906;
*Lactobacillus paracasei* LB113R, which is deposited as DSM 32907;
*Lactobacillus plantarum* LB244R, which is deposited as DSM 32996;
*Lactobacillus paracasei* LB116R, which is deposited as DSM 32908;
*Enterococcus faecium* LB276R, which is deposited as DSM 32997;
*Lactobacillus plantarum* LB316R, which is deposited as DSM 33091;
*Leuconostoc mesenteriodes* LB341R;
*Leuconostoc mesenteriodes* LB349R, which is deposited as DSM 33093;
*Lactobacillus plantarum* LB356R, which is deposited as DSM 33094;
*Lactobacillus plantarum* LB312R, which is deposited as DSM 33098;

In an even further preferred embodiment of the present invention the genetic homology may be at least 96%; such as at least 97%; e.g. at least 98%; such as at least 99%; e.g. at least 99.5%; such as at least 99.8%; e.g. at least 99.9%; such as 100% (identical) to one or more of the bacterial strains selected from the group consisting of:

*Weissella viridescens* LB10G, which is deposited as DSM 32906;
*Lactobacillus paracasei* LB113R, which is deposited as DSM 32907;
*Lactobacillus plantarum* LB244R, which is deposited as DSM 32996;
*Lactobacillus paracasei* LB116R, which is deposited as DSM 32908;
*Enterococcus faecium* LB276R, which is deposited as DSM 32997;
*Lactobacillus plantarum* LB316R, which is deposited as DSM 33091;
*Leuconostoc mesenteriodes* LB349R, which is deposited as DSM 33093;
*Lactobacillus plantarum* LB356R, which is deposited as DSM 33094;
*Lactobacillus plantarum* LB312R, which is deposited as DSM 33098;

In yet a preferred embodiment of the present invention the bacterial strains may be selected from the group consisting of:

*Weissella viridescens* LB10G, which is deposited as DSM 32906;
*Lactobacillus paracasei* LB113R, which is deposited as DSM 32907;
*Lactobacillus plantarum* LB244R, which is deposited as DSM 32996;
*Lactobacillus paracasei* LB116R, which is deposited as DSM 32908;
*Enterococcus faecium* LB276R, which is deposited as DSM 32997;
*Lactobacillus plantarum* LB316R, which is deposited as DSM 33091;
*Leuconostoc mesenteriodes* LB341R;
*Leuconostoc mesenteriodes* LB349R, which is deposited as DSM 33093;
*Lactobacillus plantarum* LB356R, which is deposited as DSM 33094;
*Lactobacillus plantarum* LB312R, which is deposited as DSM 33098;

In yet a preferred embodiment of the present invention the bacterial strains may be selected from the group consisting of:

*Weissella viridescens* LB10G, which is deposited as DSM 32906;
*Lactobacillus paracasei* LB113R, which is deposited as DSM 32907;
*Lactobacillus plantarum* LB244R, which is deposited as DSM 32996;

*Lactobacillus paracasei* LB116R, which is deposited as DSM 32908;
*Enterococcus faecium* LB276R, which is deposited as DSM 32997;
*Lactobacillus plantarum* LB316R, which is deposited as DSM 33091;
*Leuconostoc mesenteriodes* LB349R, which is deposited as DSM 33093;
*Lactobacillus plantarum* LB356R, which is deposited as DSM 33094;
*Lactobacillus plantarum* LB312R, which is deposited as DSM 33098;

It was surprisingly found that the at least one lactic acid bacterium according to the present invention show strong effects against the transfer between a surface of a first subject and surface of a second subject while being non-pathogenic and not causing any damage to or influence on the gut microbiota.

The present invention discloses a composition and a method for using probiotic bacteria to inhibit transfer of MRSA.

The present invention provides a composition for the prevention of an infection, comprising an effective concentration (a therapeutically effective amount) of one or more species or strains of probiotic bacteria, such as *Lactobacillus* spp., within a pharmaceutically-acceptable carrier suitable for administration to a surface, e.g. for topical administration on the skin of a mammal, wherein said *Lactobacillus* strain possesses the ability to inhibit pathogens and thereby reduce both the colonization rate and the potential physiologically deleterious effects due to the colonization and transfer of said pathogenic bacteria.

The composition according to the present invention may preferably comprise a pharmaceutically or cosmetically acceptable vehicle or excipient.

It is preferable for the composition to be present in solid, liquid, viscous form or as a dried form.

In an embodiment the at least one lactic acid bacterium and/or the composition according to the present invention may be freeze-dried.

The composition according to the present invention may comprise a cryoprotectant.

The composition may preferably be formulated into an emulsion; an oil; a gum; a paste; a powder; a talc; a lotion; a custard; a foam; a crème; a gel; an ointment; a suspension; a mist; a spray; or a liquid.

In a preferred embodiment, the present invention relates to a powder composition for skin of either humans or animals.

In a further preferred embodiment, the powder composition may comprise hydrated magnesium silicate (talc) and at least one lactic acid bacterium according to the present invention.

In an even further preferred embodiment, the powder composition may comprise hydrated magnesium silicate, at least one carbonhydrate, and at least one lactic acid bacterium according to the present invention.

The composition may advantageously comprise probiotics, prebiotics, antimicrobials, antibiotics or other active antibacterial substances. Furthermore, the composition according to the present invention may comprise one or more of the following substances selected from antioxidants, vitamins, coenzymes, fatty acids, amino acids and cofactors.

In another embodiment of the present invention, the at least one lactic acid bacterium may be combined with a therapeutically-effective dose of an antibiotic. Either as a co-treatment or following an antibiotic therapy. The antibiotic may be Vancomycin; Gentamicin; Oxacillin; Tetracyclines; Nitroflurantoin; Chloramphenicol; Clindamycin; Trimethoprim-sulfamethoxasole; a member of the Cephlosporin antibiotic family (e.g., Cefaclor, Cefadroxil, Cefixime, Cefprozil, Ceftriaxone, Cefuroxime, Cephalexin, Loracarbef, and the like); a member of the Penicillin family of antibiotics (e.g., Ampicillin, Amoxicillin/Clavulanate, Bacampicillin, Cloxicillin, Penicillin VK, and the like); with a member of the Fluoroquinolone family of antibiotics (e.g., Ciprofloxacin, Grepafloxacin, Levofloxacin, Lomefloxacin, Norfloxacin, Ofloxacin, Sparfloxacin, Trovafloxacin, and the like); fusidic acid or a member of the Macrolide antibiotic family (e.g., Azithromycin, Erythromycin, and the like).

In an embodiment of the present invention at least one subject may be a human.

In a further embodiment of the present invention at least one subject may be an animal, such as a pig.

In yet an embodiment of the present invention the at least one subject may be a hard surface.

A preferred embodiment of the present invention relates to a method for reducing the transfer of a pathogenic microorganism between a surface of a first subject and a surface of a second subject by administrating a composition having an effective amount of at least one lactic acid bacterium.

In an embodiment of the present invention the first subject may be a first mammal or a first fabric material.

In yet an embodiment of the present invention the second subject may be selected from a second mammal, a hard surface selected from a metal material; a steel material; a wood material; a plastic material; a rubber material; a glass material; a second fabric material and/or a silicone material.

Preferably, the first mammal and/or the second mammal may be a human; a pet; or a livestock animal.

The human may be infants, toddlers, children, healthy persons, the elderly, immunosuppressed people, people with single-occurrence or recurring *Staphylococcus aureus* infections and/or people with antibiotic resistant bacterial infections. The invention may also be used for animals including pets and livestock.

In an embodiment of the present invention the administration of the composition may be as a topical treatment of the skin and/or an oral supplement.

The at least one of the first subject and/or the second subject may be a pet or a livestock animal having an effective amount of at least one lactic acid bacterium administrated as a topical treatment of the skin and/or an oral feed supplement.

In an embodiment of the present invention wherein a method may be provided to reduce transfer of a resistant pathogen between subjects (such as a first subject and a second subject) in a stable wherein the composition of the invention is administrated to at least one of the subjects, preferably to the surface of a subject, a first or second subject.

In a further embodiment of the present invention wherein a method may be provided for reducing transfer of a resistant pathogen between subjects (such as a first subject and a second subject) in a stable wherein the composition of the invention is administrated to livestock feed and/or water and/or skin of the livestock animal.

In an even further embodiment of the present invention wherein a method may be provided for reducing the transfer of a resistant pathogen between subjects (such as a first subject and a second subject) in a stable wherein the composition of the invention may be administrated to the hard surfaces or equipment in the stable.

A method may be provided according to the present invention for reducing the transfer of a resistant pathogen between subjects (such as a first subject and a second subject) in a hospital or nursery home wherein the composition of the invention is administrated to at least one of the subjects.

In an embodiment of the present invention a method may be provided to reduce transfer of a resistant pathogen between subjects (such as a first subject and a second subject) in a hospital or nursery home wherein the composition of the invention is administrated to patients as a product for oral consumption and/or topical application.

In another embodiment of the present invention a method may be provided to reduce transfer of a resistant pathogen between subjects (such as a first subject and a second subject) in a hospital or nursery home wherein the composition of the invention is administrated to the hard surfaces or equipment in the hospital or nursery home.

The composition may comprise the at least one lactic acid bacterium in viable form; killed/dead form; lysate form; or fragments hereof. Preferably, the composition may comprise the at least one lactic acid bacterium in viable form; killed/dead form; or lysate form. Even more preferably, the composition may comprise the at least one lactic acid bacterium in viable form or killed/dead form.

The at least one lactic acid bacterium may advantageously be present in viable or killed/dead form in the composition. In an embodiment of the present invention the at least one lactic acid bacterium may be provided in an encapsulated, micro-encapsulated, spray-dried and/or lyophilized form. In a further embodiment of the present invention the at least one lactic acid bacterium may be present in the form of a cell lysate.

Preferably, the at least one lactic acid bacterium may be present in the composition in an amount by weight of 0.001 wt % to 20 wt %, preferably 0.005 wt % to 10 wt %, especially preferably 0.01 wt % to 5 wt %.

In an embodiment of the present invention involves the administration of from approximately $1\times10^3$ to $1\times10^{14}$ CFU of viable bacteria per day, more preferably from approximately $1\times10^5$ to $1\times10^{10}$, and most preferably from approximately $5\times10^8$ to $1\times10^9$ CFU of viable bacteria per day.

Where the condition to be treated involves antibiotic resistant pathogens and the patient is an adult, the typical dosage is approximately $1\times10^2$ to $1\times10^{14}$ CFU of viable bacteria per day, preferably from approximately $1\times10^8$ to $1\times10^{10}$, and more preferably from approximately $2.5\times10^8$ to $1\times10^{10}$ CFU of viable bacteria per day. Where the subject to be treated is an infant over 6 months old, the dosage is typically $1\times10^6$ to $1\times10^9$ CFU of viable bacteria per day preferably from approximately $5\times10^4$ to $2.5\times10^5$ CFU and more preferably from approximately $1\times10^5$ to $2\times10^5$ CFU of viable bacteria per day.

In an embodiment of the present invention the decrease and/or inhibition of transfer of a pathogenic microorganism includes decrease and/or inhibition of transfer of antibiotic resistant Gram-positive pathogens. The antibiotic resistant Gram-positive pathogens may be *Staphylococcus aureus, Staphylococcus pyogenes, Clostridium perfingens, Clostridium dificile, Clostridium botulinum, Clostridium tributrycum, Clostridium sporogenes, Enterococccus faecalis, Enterococcus faecium*, and various other significant species of antibiotic resistant pathogens or combinations thereof.

The pathogenic microorganism may be resistant to at least one of the following antibiotics; Vancomycin, penicillin, metronidazole, fusidic acid and/or fidaxomicin.

The pathogenic microorganism may relate to a microorganism or an analog thereof, a fragment, a derivative or combination thereof wherein the ability to inhibit transfer of least one pathogenic microorganism exists even after a biological, chemical or physical treatment.

In an embodiment of the present invention the analogue thereof may be at least one lactic acid bacteria having a genetic homology of at least 95% to one or more of the bacterial strains selected from the group consisting of:
  *Weissella viridescens* LB10G, which is deposited as DSM 32906;
  *Lactobacillus paracasei* LB113R, which is deposited as DSM 32907;
  *Lactobacillus plantarum* LB244R, which is deposited as DSM 32996;
  *Lactobacillus paracasei* LB116R, which is deposited as DSM 32908;
  *Enterococcus faecium* LB276R, which is deposited as DSM 32997;
  *Lactobacillus plantarum* LB316R, which is deposited as DSM 33091;
  *Leuconostoc mesenteriodes* LB341R;
  *Leuconostoc mesenteriodes* LB349R, which is deposited as DSM 33093;
  *Lactobacillus plantarum* LB356R, which is deposited as DSM 33094;
  *Lactobacillus plantarum* LB312R, which is deposited as DSM 33098;

In an embodiment of the present invention the analogue thereof may be at least one lactic acid bacteria having a genetic homology of at least 95% to one or more of the bacterial strains selected from the group consisting of:
  *Weissella viridescens* LB10G, which is deposited as DSM 32906;
  *Lactobacillus paracasei* LB113R, which is deposited as DSM 32907;
  *Lactobacillus plantarum* LB244R, which is deposited as DSM 32996;
  *Lactobacillus paracasei* LB116R, which is deposited as DSM 32908;
  *Enterococcus faecium* LB276R, which is deposited as DSM 32997;
  *Lactobacillus plantarum* LB316R, which is deposited as DSM 33091;
  *Leuconostoc mesenteriodes* LB349R, which is deposited as DSM 33093;
  *Lactobacillus plantarum* LB356R, which is deposited as DSM 33094;
  *Lactobacillus plantarum* LB312R, which is deposited as DSM 33098;

In a further embodiment of the present invention the decreasing or inhibition of the transfer of a pathogenic microorganism may be provided at a pH in the range of pH 3-8, such as in the range of pH 4-7, e.g. in the range of pH 5-6.

In an embodiment of the present invention the composition may be used to prepare a pharmaceutical drug that is beneficial for the treatment or prevention of transfer of a pathogenic microorganism.

The composition according to the present invention may be used as a probiotic. Furthermore, the composition according to the present invention may be used curatively or prophylactically. In an embodiment of the present invention the composition may be used to decrease the transfer of HA-MRSA and/or CA-MRSA and/or LA-MRSA.

The at least one lactic acid bacterium according to the invention are preferably in isolated or purified form, where the term "isolated" means in particular that the at least one lactic acid bacterium are derived from their culture medium including their natural medium. The term "purified" is not restricted to absolute purity.

It is preferable that in addition to the microorganisms according to the invention in a viable form, killed form of the at least one lactic acid bacterium according to the invention are also included within the scope of the present invention.

Suitable methods for killing the at least one lactic acid bacterium (e.g., biological, chemical or physical killing methods) are sufficiently familiar to those skilled in the art. In the present case, however, the at least one lactic acid bacterium may also be used in lyophilized form. The killed forms of the at least one lactic acid bacterium may include the fermentation broth and any metabolites present in said fermentation broth.

The terms "killed" or "dead" relates to inactivated lactic acid bacteria incapable of cell division and without any metabolic activity. Dead or killed lactic acid bacteria may have intact or ruptured cell membranes.

"Lysates", "derivatives", "analogs", "fractions" or "extracts" may be obtained from dead or killed lactic acid bacteria. These lysates, fractions, derivative, analogs, and extracts preferably have the properties of decreasing the transfer of a pathogenic microorganism between a surface of a first subject and a surface of a second subject, where "lysate" as well as the term "extract" refers in particular to a solution or suspension in an aqueous medium of the cells of the microorganism according to the invention and comprises, for example, macromolecules such as DNA, RNA, proteins, peptides, lipids, carbohydrates, etc. as well as cell detritus. The lysate preferably includes the cell wall or cell wall constituents including binding receptors. Methods of producing lysates are sufficiently well known to those skilled in the art and includes, for example, the use of a "French press" or enzymatic lysis, a ball mill with glass beads or iron beads. Cells can be broken open by enzymatic, physical or chemical methods. Examples of enzymatic cell lysis may include individual enzymes as well as enzyme cocktails, for example, proteases, proteinase K, lipases, glycosidases; chemical lysis may be induced by ionophores, detergents such as SDS, acids or bases; physical methods may also be implemented by using high pressures such as the French press, osmolarities, temperatures or alternating between heat and cold. Furthermore chemical, physical and enzymatic methods may of course be combined.

"Killed", "dead", "derivatives", "analogs", "extracts" or "fractions" according to the invention may preferably have the same coaggregation properties as the at least one lactic acid bacterium described herein.

A fragment of the microorganisms according to the invention may be a part of the cells, e.g., cell membrane, macromolecules such as DNA, RNA, proteins, peptides, lipids, carbohydrates, etc. as well as cell detritus.

Derivative may be genetically altered variants, for example, by recombinant DNA technologies (cloning, sequencing, transformation of recombinant nucleic acids) as well as physical mutagenesis, for example, by ultraviolet radiation but also through chemical agents such as with ethyl methane sulfonate (EMS) or adaptive laboratory evolution. Changes in the positive properties can be selected. Genetically altered derivatives contain cells of the microorganisms according to the invention and retain recombinant nucleic acids in their bacterial chromosome and/or plasmids. Modifications through point mutations may also induce effects on the expression/transcription/translation as well as spontaneous mutations even without any direct genetic manipulation. Derivatives of the at least one lactic acid bacterium may be in viable form or in dead/killed form.

Analogs or fragments may include thermally killed (dead) or lyophilized forms of the at least one lactic acid bacterium according to the invention which retain their properties according to the invention or even improve them, e.g. by enlarging the surface area. Cells after lyophilization (freeze drying) are still viable under some circumstances. These cells can be killed by special storage processes at different temperatures. Dead cells may have intact or ruptured cell membranes, for example, but do not have any metabolic activity.

Methods of producing killed cells may include, for example, a treatment with glass beads, where the effect of the shearing forces between the cells and the glass beads result in rupture of the cell. Other physical methods such as French press, high-pressure homogenization, ball mill or freeze-thaw processes and autoclaving result in killing of cells and also lead to fragments of the microorganisms according to the invention, as do UV irradiation, autolysis methods or special storage processes at different temperatures.

It will be clear to those skilled in the art that here, as well as in all the statements of range given in the present invention, characterized by such terms as "about" or "approximately," that the precise numerical range need not be indicated with expressions such as "about" or "approx." or "approximately," but instead even minor deviations up or down with regard to the number indicated are still within the scope of the present invention. In an embodiment of the present invention, the minor deviation may include a 5% deviation or less, such as a 4% deviation or less, e.g. a 3% deviation or less, such as a 2% deviation or less, e.g. a 1% deviation or less.

In an embodiment of the present invention, a biologically pure culture of *Lactobacillus* sp. may be provided.

Preferably, a probiotic composition may be provided comprising, as an active ingredient, the at least one lactic acid bacterium according to the present invention and a carrier or diluent. Preferably, the probiotic composition may be suitable for decreasing or inhibiting transfer of pathogenic microorganisms.

In the present context the term "subject" as used herein may relate to mammals, avians or surfaces.

Mammals may include, but are not limited to, humans, primates, livestock animals, farm animals, sport animals, rodents and pets. Non-limiting examples of non-human animal subjects include rodents such as mice, rats, hamsters, and guinea pigs; rabbits; dogs; cats; sheep; pigs; piglets; sows; poultry; turkeys; broilers; minks; goats; cattle; horses; and non-human primates such as apes and monkeys.

Surfaces included as a subject may be the surfaces in stables, stalls, slaughterhouses, animal transport vehicles, equipment used in livestock production, areas in pet care, cat litter, hospitals, equipment used in hospitals, including hard surfaces and toilet facilities.

A "carrier" is a subject colonized or contaminated with a pathogen microorganism. The carrier can be a hard surface, a healthy mammal or an infected mammal.

In the present context the term "effective amount" of a substance relates to the amount sufficient to effect beneficial or desired results, including clinical results, and, as such, an "effective amount" depends upon the context in which it is being applied. In the context of administering a composition to decrease the risk of transfer of MRSA between subjects. The decrease can be a 10 percent, 20 percent, 30 percent, 40 percent, 50 percent, 60 percent, 70 percent, 80 percent, 90 percent, 95 percent, 98 percent, 99 percent or 99.9 percent decrease in severity of MRSA, or likelihood of becoming infected. An effective amount can be administered as a composition in one or more administrations.

The probiotic composition may be applied to hard surface subjects using various methods including: spraying, brushing, rubbing (as for example with a disposable wipe), or use of an applicator (e.g. roller), or; by dipping, submerging or rolling the contact surface in the probiotic composition.

In an embodiment of the present invention the composition may be applied in more than one type of administration. Incorporated into the feed or food for a mammal and/or applied to the skin and/or to a hard surface in either a stable, stall or hospital setting. In a further embodiment of the present invention the composition is applied in more than one type of administration. Eg. Both incorporated into the feed or food for a mammal and applied to the skin of a mammal.

In yet an embodiment of the present invention the composition further comprises a prebiotic. In the present context the term "Prebiotics" relates to non-digestible food components that increase the growth of specific microorganisms in the gastrointestinal tract. "Synbiotics" are compositions comprising at least one probiotic and at least one prebiotic. Such compositions are understood to encourage the growth of beneficial bacteria (e.g. the probiotic). Thus, powerful synbiotics are based on a combination of specific lactic acid bacteria according to the present invention with carefully selected prebiotics. They can lead to an important health benefit to a mammal.

Prebiotics refer to chemical products that induce the growth and/or activity of commensal microorganisms (e.g., bacteria and fungi) that contribute to the well-being of their host. Prebiotics are nondigestible carbohydrates that pass undigested through the upper part of the gastrointestinal tract and stimulate the growth and/or activity of advantageous bacteria that colonize the large bowel or skin microorganisms.

Some oligosaccharides that are used as prebiotics are fructooligosaccharides (FOS), xylooligosaccharides (XOS), polydextrose, pectins, galactooligosaccharides (GOS) or human milk oligo saccharides (HMO). Moreover, disaccharides like lactulose or some monosaccharides such as tagatose can also be used as prebiotics.

The other active ingredient (or other ingredients) is not limited in any way. In a preferred aspect, at least one prebiotic compound is comprised in the composition of the invention, i.e. as other ingredient. In a very broad concept, prebiotics are all those food sources which can be metabolized by probiotics. Preferably prebiotics are non-digestible or poorly digestible by a mammal. Thus, following uptake by the mammal, the non-digestible prebiotics can pass through the small intestine and enter the large intestine to stimulate the growth of the probiotics in this compartment. Prebiotics can thus serve as a food source for probiotics. It is believed that the prebiotics, many of which are non-digestible carbohydrates, promote the growth of probiotics. Prebiotics may be naturally found for example in cabbage, onions, whole grains, bananas, garlic, honey, leeks, artichokes, fortified foods and beverages, as well as dietary supplements. Prebiotics are well known in the art and when used in the present invention there is no particular limitation of the prebiotic as such. In preferred embodiments however the at least one prebiotic product in the composition is selected from the following compounds and compositions: non-digestible carbohydrates, beta-glucans, mannan-oligo-saccharides, inulin, oligofructose, human milk oligosaccharides (HMO), galactooligosaccharides (GOS), lactulose, lactosucrose, galactotriose, fructo-oligosaccaride (FOS), cellobiose, cellodextrins, cylodextrins, maltitol, lactitol, glycosilsucrose, Vitamin E or a variant thereof (wherein the variants are selected from alfa, beta, gamma, delta tocoferols, tocotrienols and tocomonoenols). Optionally, mannan-oligosaccharides and/or inulin may be preferred.

In an embodiment of the present invention the composition further comprises in addition to the at least one lactic acid bacteria having a genetic homology of at least 95% to one or more of the bacterial strains selected from the group consisting of:

*Weissella viridescens* LB10G, which is deposited as DSM 32906;

*Lactobacillus paracasei* LB113R, which is deposited as DSM 32907;

*Lactobacillus plantarum* LB244R, which is deposited as DSM 32996;

*Lactobacillus paracasei* LB116R, which is deposited as DSM 32908;

*Enterococcus faecium* LB276R, which is deposited as DSM 32997;

*Lactobacillus plantarum* LB316R, which is deposited as DSM 33091;

*Leuconostoc mesenteriodes* LB341R;

*Leuconostoc mesenteriodes* LB349R, which is deposited as DSM 33093;

*Lactobacillus plantarum* LB356R, which is deposited as DSM 33094;

*Lactobacillus plantarum* LB312R, which is deposited as DSM 33098;

at least one further active ingredient.

In an embodiment of the present invention the composition further comprises in addition to the at least one lactic acid bacteria having a genetic homology of at least 95% to one or more of the bacterial strains selected from the group consisting of:

*Weissella viridescens* LB10G, which is deposited as DSM 32906;

*Lactobacillus paracasei* LB113R, which is deposited as DSM 32907;

*Lactobacillus plantarum* LB244R, which is deposited as DSM 32996;

*Lactobacillus paracasei* LB116R, which is deposited as DSM 32908;

*Enterococcus faecium* LB276R, which is deposited as DSM 32997;

*Lactobacillus plantarum* LB316R, which is deposited as DSM 33091;

*Leuconostoc mesenteriodes* LB349R, which is deposited as DSM 33093;

*Lactobacillus plantarum* LB356R, which is deposited as DSM 33094;

*Lactobacillus plantarum* LB312R, which is deposited as DSM 33098;

at least one further active ingredient.

In an embodiment the "at least one further active ingredient" may be at least one further probiotic microorganism selected from the group consisting of bacteria, yeasts or molds.

In an embodiment of the present invention the probiotic microorganismmay be selected from:

*Bifidobacterium lactis* DSM10140, *B. lactis* LKM512, *B. lactis* DSM 20451, *Bifidobacterium bifidum* BB-225, *Bifidobacterium adolescentis* BB-102, *Bifidobacterium breve* BB-308, *Bifidobacterium longum* BB-536 from Zaidanhojin Nihon Bifizusukin Senta (Japan *Bifidus* Bacteria Center), *Bifidobacterium* NCIMB 41675 described in EP2823822. *Bifidobacterium bifidum* BB-225, *Bifidobacterium adolescentis* BB-102, *Bifidobacterium breve* BB-308, *Bifidobacterium lactis* HN019 (Howaru) available from DuPont Nutrition Biosciences ApS, *Bifidobacterium lactis* DN 173 010 available from Groupe Danone, *Bifidobacterium lactis* Bb-12 available from Chr. Hansen A/S, *Bifidobacterium lactis* 420 available from DuPont Nutrition Biosciences ApS, *Bifidobacterium breve* Bb-03, *B. lactis* BI-04, *B. lactis* Bi-07 available from DuPont Nutrition Biosciences ApS, *Bifidobacterium bifidum* Bb-02, *Bifidobacterium bifidum* Bb-06, *Bifidobacterium longum* KC-1 and *Bifidobacterium longum* 913 (DuPont Nutrition Biosciences ApS), *Bifidobacterium breve* M-16V (Morinaga) and/or a *Lactobacillus* having a probiotic effect and may be any of the following strains; *Lactobacillus rhamnosus* LGG (Chr. Hansen), *Lactobacillus acidophilus* NCFM (DuPont Nutrition Biosciences ApS), *Lactobacillus bulgaricus* 1260 (DuPont Nutrition Biosciences ApS), *Lactobacillus paracasei* Lpc-37 (DuPont Nutrition Biosciences ApS), *Lactobacillus rhamnosus* HN001 (Howaru) available from DuPont Nutrition Biosciences ApS, *Streptococcus thermophilus* 715 and *Streptococcus thermophilus* ST21 available from DuPont Nutrition Biosciences ApS, *Lactobacillus paracasei* subsp. *paracasei* CRL431 (ATCC 55544), *Lactobacillus paracasei* strain F-19 from Medipharm, Inc. *L. paracasei* LAFTI L26 (DSM Food Specialties, the Netherlands) and *L. paracasei* CRL 431 (Chr. Hansen), *Lactobacillus acidophilus* PTA-4797, *L. salivarius* Ls-33 and *L. curvatus* 853 (DuPont Nutrition Biosciences ApS). *Lactobacillus casei* ssp. *rhamnosus* LC705 is described in FI Patent 92498, Valio Oy, *Lactobacillus* DSM15527 (Bifodan), *Lactobacillus* DSM15526 (Bifodan), *Lactobacillus rhamnosus* GG (LGG) (ATCC 53103) is described in U.S. Pat. No. 5,032,399 and *Lactobacillus rhamnosus* LC705 (DSM 7061), Propionic acid bacterium eg. *Propionibacterium freudenreichii* ssp. *shermanii* PJS (DSM 7067) described in greater details in FI Patent 92498, Valio Oy, *Nitrosomonas eutropha* D23 (ABIome), *Staphylococcus hominis* strains A9, C2, AMT2, AMT3, AMT4-C2, AMT4-GI, and/or AMT4-D12. (all from Matrisys Bioscience), *Staphylococcus epidermidis* strains M034, M038, All, AMT1, AMT5-C5, and/or AMT5-G6 (all from Matrisys Bioscience), *L. plantarum* YUN-V2.0 (BCCM LMG P-29456), *L. pentosus* YUN-V1.0 (BCCN LMG P-29455), *L. rhamnosus* YUN-S1.0 (BCCM LMG P-2961) and/or any combinations hereof.

In yet an embodiment of the present invention a food additive comprising as an active ingredient, the at least one lactic acid bacterium according to the present invention, and a carrier suitable for human consumption may be provided.

Preferably the product for oral consumption may comprise from $1 \times 10^6$ to $1 \times 10^{14}$ Colony Forming Units (CFU) per serving, or per dose.

The present invention relates to probiotic treatment of MRSA is an alternative to antibiotic treatments. Probiotics are GRAS microorganisms and advantageously over antibiotics as no resistance development or toxic side effects has been observed for lactic acid bacteria.

In an embodiment of the present invention the effect of the composition according to the present invention and the method according to the present invention does not involve a rinsing step for removing the biofilm from the surface before adding the at least one lactic acid bacterium.

Deposit of Biological Material

The following biological material, microorganisms, have been deposited at the with the German Collection for Microorganisms and Cell Cultures located at Inhoffenstrasse 7B, 38124 Braunschweig, Germany:

*Weissella viridescens* LB10G, which is deposited as DSM 32906 on Aug. 28, 2018;
*Lactobacillus paracasei* LB113R, which is deposited as DSM 32907 on Aug. 28, 2018;
*Lactobacillus plantarum* LB244R, which is deposited as DSM 32996 on Dec. 13, 2018;
*Lactobacillus paracasei* LB116R, which is deposited as DSM 32908 on Aug. 28, 2018;
*Enterococcus faecium* LB276R, which is deposited as DSM 32997 on Dec. 13, 2018;
*Lactobacillus plantarum* LB316R, which is deposited as DSM 33091 on Apr. 10, 2019;
*Leuconostoc mesenteriodes* LB349R, which is deposited as DSM 33093 on Apr. 10, 2019;
*Lactobacillus plantarum* LB356R, which is deposited as DSM 33094 on Apr. 10, 2019;
*Lactobacillus plantarum* LB312R, which is deposited as DSM 33098 on Apr. 10, 2019;

It should be noted that embodiments and features described in the context of one of the aspects of the present invention also apply to the other aspects of the invention.

The invention will now be described in further details in the following non-limiting examples.

EXAMPLES

Example 1 Strain Screening Identification

Samples

For identification and selection of bacterial strain according to the invention, a strain collection of lactic acid bacteria (LAB) was established. Samples from different origins, such as homemade sauerkraut, kimchi and healthy human donor samples (vaginal, oral, anal, skin) were collected for isolation of at least 995 lactic acid bacteria. The samples were collected on Man Rogosa Sharp (MRS, Sigma-Aldrich) broth and agar cultured anaerobically at 37° C. overnight or until colony formation. The isolates are plated and subcultured until pure colonies were obtained. The pure colonies are stored in MRS broth with 25% glycerol at −80° C. for future use. Strains were identified using 16S rRNS Sanger sequencing standard methods.

Example 2 Co-Culture Assay/Competition Assay

Competition between bacterial strains and *Staphylococcus aureus* was determined (Dowarah, R., et al. 2018, Selection and characterization of probiotic lactic acid bacteria and its impact on growth, nutrient digestibility, health and antioxidant status in weaned piglets. PLoS ONE, 13 (3), Khare, A., & Tavazoie, S. (2015). Multifactorial Competition and Resistance in a Two-Species Bacterial System. PLoS Genetics, 11 (12), 1-21.)

*Staphylococcus aureus* subsp. *aureus* COL (CCOS461), *Staphylococcus aureus* CC398 (SSI strain 08S00974) and *Staphylococcus aureus* US300 (ATCC BAA-1717) were used as MRSA test organisms. *S. aureus* were cultured in Brain Heart Infusion (BHI) broth.

The cell density of overnight culture of *S. aureus* and isolates was adjusted according to an optical density at 600 nm (OD600) of 1 and harvested by centrifugation (6.000 rpm for two minutes). The cell pellet is washed twice in phosphate buffered saline (1×PBS) and resuspended in 1×PBS. One milliliter of each cell suspensions is mixed in 50 ml of BHI broth and co-incubated at 37° C. for 24 hours, while monocultures of MRSA and LAB are used as controls. At time 0, 2 hours, 6 hours, 10 hours and 24 hours, serial dilutions of the cell solutions are plated out on nutrient agar plates to count forming colonies. MRS agar was used for LAB isolates and Mannitol Salt Phenol Red Agar (Sigma-Aldrich) was used for *Staphylococcus aureus*.

17 strains of LAB from the collection of 450 strains were identified as being able to out-compete growth of both all three tested MRSA strains.

Example 3 Determination of Transfer Between Subjects

Transfer of a pathogenic bacteria between two subjects were determined by a co-culture assay. The cell density of overnight cultures of *S. aureus* and bacterial strain isolate is adjusted according to an optical density at 600 nm (OD600) of 1 and harvested by centrifugation (6.000 rpm for two minutes). The cell pellet is washed twice in phosphate buffered saline (1×PBS) and resuspended in 1×PBS to a cell concentration of approximately $1 \times 10^4$ CFU/ml. The two cell suspensions were mixed 1:1 and 0.2 ml was spread on BHI agar plates and allowed to dry in sterile air for 5 min. Monocultures of MRSA and LAB are used as controls, for control plates the cell suspension were mixed 1:1 with sterile PBS buffer and 0.2 ml was spread on BHI agar plates and allowed to dry in sterile air for 5 min.

5 ml of sterile PBS was absorbed by a sterile round filter type A.G.F 118 (D 9 cm) and placed on top of the agar plate securing a uniform contact between the agar and the humidified paper. After 5 second contact the paper was transferred to a *Staphylococcus* selective agar plate (Mannitol Salt Phenol Red Agar), the filter was placed on the agar securing a uniform contact between the filter paper and the agar for 5 seconds. The filter paper was removed, and the agar plates were incubated at 37° C. for 24 hours (transfer plate). The number of bacteria being transferred from one agar plate to another agar plate was counted and the decrease in transfer was determined relative to transfer of MRSA from a control with no LAB.

The transfer between two subjects was determined by counting the number of colony-forming units (CFU) and comparing the number from co-suspensions with the monoculture controls. All transfer test was done in triplets.

NC=CFU counts of MRSA on transfer plates of MRSA control plates

NLAB=CFU counts of MRSA on transfer plates of the co-plated plates with both LAB and MRSA.

Decrease in transfer=[*NC*−NLAB]/[*NC*]×100%

Results are shown in table 1 with the decrease in transfer calculated as described above.

| Bacterial strains | MRSA | Decrease in transfer between two subjects* |
|---|---|---|
| *Weissella viridescens* LB10G | *S. aureus* COL | 99% |
| *Weissella viridescens* LB10G | *S. aureus* CC398 | 91% |
| *Weissella viridescens* LB10G | *S. aureus* US300 | 81% |
| *Lactobacillus paracasei* LB113R | *S. aureus* COL | 98% |
| *Lactobacillus paracasei* LB113R | *S. aureus* CC398 | 100% |
| *Lactobacillus paracasei* LB113R | *S. aureus* US300 | 78% |
| *Lactobacillus paracasei* LB116R | *S. aureus* COL | 90% |

-continued

| Bacterial strains | MRSA | Decrease in transfer between two subjects* |
|---|---|---|
| *Lactobacillus paracasei* LB116R | *S. aureus* CC398 | 87% |
| *Lactobacillus paracasei* LB116R | *S. aureus* US300 | 85% |

*Average from triplet determination

Results are shown in table 2 with the decrease in transfer of MRSA US300 calculated as described above.

| Bacterial strains | Decrease in transfer between two subjects (%)* |
|---|---|
| *Weissella viridescens* LB10G | 81% |
| *Lactobacillus paracasei* LB113R | 78% |
| *Lactobacillus plantarum* LB244R | 92% |
| *Lactobacillus paracasei* LB116R | 85% |
| *Enterococcus faecium* LB276R | 77% |
| *Lactobacillus plantarum* LB312R | 80% |
| *Lactobacillus plantarum* LB316R | 89% |
| *Leuconostoc mesenteroides* LB341R | 74% |
| *Leuconostoc mesenteroides* LB349R | 91% |
| *Lactobacillus plantarum* LB356R | 88% |

*Weissella viridescens* LB10G, which is deposited as DSM 32906;

*Lactobacillus paracasei* LB113R, which is deposited as DSM 32907;

*Lactobacillus plantarum* LB244R, which is deposited as DSM 32996;

*Lactobacillus paracasei* LB116R, which is deposited as DSM 32908;

*Enterococcus faecium* LB276R, which is deposited as DSM 32997;

*Lactobacillus plantarum* LB316R, which is deposited as DSM 33091;

*Leuconostoc mesenteriodes* LB341R;

*Leuconostoc mesenteriodes* LB349R, which is deposited as DSM 33093;

*Lactobacillus plantarum* LB356R, which is deposited as DSM 33094;

*Lactobacillus plantarum* LB312R, which is deposited as DSM 33098;

The invention claimed is:

1. A composition comprising at least one isolated lactic acid bacterium, wherein the at least one lactic acid bacterium in the composition is freeze-dried, the at least one isolated lactic acid bacterium has a genetic homology of at least 95% to a 16S rRNA gene of one or more of the bacterial strains selected from the group consisting of:

*Weissella viridescens* LB10G, which is deposited as DSM 32906,

*Lactobacillus paracasei* LB113R, which is deposited as DSM 32907,

*Lactobacillus plantarum* LB244R, which is deposited as DSM 32996,

*Lactobacillus paracasei* LB116R, which is deposited as DSM 32908,

*Enterococcus faecium* LB276R, which is deposited as DSM 32997,

*Lactobacillus plantarum* LB316R, which is deposited as DSM 33091,

*Leuconostoc mesenteriodes* LB341R,

*Leuconostoc mesenteriodes* LB349R, which is deposited as DSM 33093,

*Lactobacillus plantarum* LB356R, which is deposited as DSM 33094, and
*Lactobacillus plantarum* LB312R, which is deposited as DSM 33098,
and the composition decreases the transfer of a pathogenic microorganism between a surface of a first subject and a surface of a second subject, wherein the composition is formulated into an emulsion; an oil; a gum; a paste; a talc; a lotion; a custard; a foam; a creme; a gel; an ointment; a suspension; a mist; or a liquid.

2. The composition according to claim 1, wherein the transfer of a pathogenic microorganism is decreased at least 10%.

3. The composition according to claim 1, wherein the pathogenic microorganism is a microorganism resistant to antibiotics.

4. The composition according to claim 3, wherein the microorganism resistant to antibiotics is a bacterium resistant to antibiotics.

5. The composition according to claim 4, wherein the bacterium resistant to antibiotics is Methicillin resistant *Staphylococcus* and/or a Vancomycin resistant *Enterococcus* species.

6. The composition according to claim 1, wherein the first subject is a first mammal or a first fabric material.

7. The composition according to claim 1, wherein the second subject is selected from a second mammal, a hard surface selected from a metal material; a steel material; a wood material; a plastic material; a rubber material; a glass material; a second fabric material and/or a silicone material.

8. The composition according to claim 7, wherein the surface of the first mammal and/or the surface of the second mammal may be the skin; the hair; the nails; and/or the hoofs.

9. The composition according to claim 1, wherein the composition further comprises a prebiotic.

10. The composition according to claim 1, wherein the composition comprises a cryoprotectant.

11. A composition comprising at least one isolated lactic acid bacterium, wherein the at least one lactic acid bacterium in the composition is freeze-dried, and the composition decreases the transfer of a pathogenic microorganism between a surface of a first subject and a surface of a second subject wherein the at least one isolated lactic acid bacterium has a genetic homology of at least 95% to a 16S rRNA gene of one or more of the bacterial strains selected from the group consisting of:
*Weissella viridescens* LB10G, which is deposited as DSM 32906,
*Lactobacillus paracasei* LB113R, which is deposited as DSM 32907,
*Lactobacillus plantarum* LB244R, which is deposited as DSM 32996,
*Lactobacillus paracasei* LB116R, which is deposited as DSM 32908,
*Enterococcus faecium* LB276R, which is deposited as DSM 32997,
*Lactobacillus plantarum* LB316R, which is deposited as DSM 33091,
*Leuconostoc mesenteriodes* LB341R,
*Leuconostoc mesenteriodes* LB349R, which is deposited as DSM 33093,
*Lactobacillus plantarum* LB356R, which is deposited as DSM 33094, and
*Lactobacillus plantarum* LB312R, which is deposited as DSM 33098.

12. The composition according to claim 11, wherein the genetic homology is at least 96% to a 16S rRNA gene of one or more of the bacterial strains selected from the group consisting of:
*Weissella viridescens* LB10G, which is deposited as DSM 32906,
*Lactobacillus paracasei* LB113R, which is deposited as DSM 32907,
*Lactobacillus plantarum* LB244R, which is deposited as DSM 32996,
*Lactobacillus paracasei* LB116R, which is deposited as DSM 32908,
*Enterococcus faecium* LB276R, which is deposited as DSM 32997,
*Lactobacillus plantarum* LB316R, which is deposited as DSM 33091,
*Leuconostoc mesenteriodes* LB349R, which is deposited as DSM 33093,
*Lactobacillus plantarum* LB356R, which is deposited as DSM 33094, and
*Lactobacillus plantarum* LB312R, which is deposited as DSM 33098.

13. The composition according to claim 11, wherein the isolated bacterial strain is selected from the group consisting of:
*Weissella viridescens* LB10G, which is deposited as DSM 32906,
*Lactobacillus paracasei* LB113R, which is deposited as DSM 32907,
*Lactobacillus plantarum* LB244R, which is deposited as DSM 32996,
*Lactobacillus paracasei* LB116R, which is deposited as DSM 32908,
*Enterococcus faecium* LB276R, which is deposited as DSM 32997,
*Lactobacillus plantarum* LB316R, which is deposited as DSM 33091
*Leuconostoc mesenteriodes* LB349R, which is deposited as DSM 33093,
*Lactobacillus plantarum* LB356R, which is deposited as DSM 33094, and
*Lactobacillus plantarum* LB312R, which is deposited as DSM 33098.

14. A method for reducing transfer of a pathogenic microorganism between a surface of a first subject and a surface of a second subject by administrating a composition of claim 1 having an effective amount of at least one lactic acid bacterium.

15. The method according to claim 14, wherein the pathogenic microorganism is a microorganism resistant to antibiotics.

16. The method according to claim 15, wherein the microorganism resistant to antibiotics is a bacterium resistant to antibiotics.

17. The method according to claim 16, wherein the bacterium resistant to antibiotics is Methicillin resistant *Staphylococcus* and/or a Vancomycin resistant *Enterococcus* specie.

18. The method according to claim 14, wherein the first subject is a first mammal or a first fabric material.

19. The method according to claim 14, wherein the second subject is selected from a second mammal, a hard surface selected from a metal material; a steel material; a wood material; a plastic material; a rubber material; a glass material; a second fabric material and/or a silicone material.

20. The composition according to claim 1, wherein the at least one isolated lactic acid bacterium is present in the composition in an amount by weight of 0.001 wt % to 20 wt %.

21. The composition according to claim 1, wherein the composition comprises a pH value in the range of pH 3-8.

22. An isolated lactic acid bacterium, wherein the lactic acid bacterium is freeze-dried and the isolated lactic acid bacterium has a genetic homology of at least 95% to a 16S rRNA gene of one or more of the bacterial strains selected from the group consisting of:
*Weissella viridescens* LB10G, which is deposited as DSM 32906,
*Lactobacillus paracasei* LB113R, which is deposited as DSM 32907,
*Lactobacillus plantarum* LB244R, which is deposited as DSM 32996,
*Lactobacillus paracasei* LB116R, which is deposited as DSM 32908,
*Enterococcus faecium* LB276R, which is deposited as DSM 32997,
*Lactobacillus plantarum* LB316R, which is deposited as DSM 33091,
*Leuconostoc mesenteriodes* LB349R, which is deposited as DSM 33093,
*Lactobacillus plantarum* LB356R, which is deposited as DSM 33094, and
*Lactobacillus plantarum* LB312R, which is deposited as DSM 33098;
wherein the isolated lactic acid bacterium is decreasing the transfer of a pathogenic microorganism between a surface of a first subject and a surface of a second subject.

23. The composition according to claim 1, wherein the at least one lactic acid bacterium is viable form; killed/dead form; or lysate form.

24. A composition comprising at least one isolated lactic acid bacterium, wherein the at least one lactic acid bacterium in the composition is present in an amount by weight of 0.001 wt % to 20 wt %; and the composition decreases the transfer of a pathogenic microorganism between a surface of a first subject and a surface of a second subject, wherein:
the at least one lactic acid bacterium in the composition is freeze-dried;
the composition is formulated into an emulsion, an oil, a gum, a paste, a powder, a talc, a lotion, a custard, a foam, a creme, a gel, an ointment, a suspension, a mist, or a liquid; or
the composition comprises a pH value in the range of pH 3-6.

25. The composition according to claim 24, wherein the transfer of a pathogenic microorganism is decreased at least 10%.

26. The composition according to claim 24, wherein the pathogenic microorganism is a microorganism resistant to antibiotics.

27. The composition according to claim 26, wherein the microorganism resistant to antibiotics is a bacterium resistant to antibiotics.

28. The composition according to claim 27, wherein the bacterium resistant to antibiotics is Methicillin resistant *Staphylococcus* and/or a Vancomycin resistant *Enterococcus* species.

29. The composition according to claim 24, wherein the composition further comprises a prebiotic.

30. The composition according to claim 24, wherein the composition is formulated into an emulsion; an oil; a gum; a paste; a powder; a talc; a lotion; a custard; a foam; a crème; a gel; an ointment; a suspension; a mist; or a liquid.

31. The composition according to claim 24, wherein the at least one isolated lactic acid bacterium is freeze-dried.

32. The composition according to claim 24, wherein the composition comprises a cryoprotectant.

33. The composition according to claim 24, wherein the composition comprises a pH value in the range of pH 3-8.

34. A composition comprising at least one isolated lactic acid bacterium, wherein the at least one lactic acid bacterium in the composition is freeze-dried, wherein the at least one isolated lactic acid bacterium has a genetic homology of at least 95% to a 16S rRNA gene of one or more of the bacterial strains selected from the group consisting of:
*Weissella viridescens* LB10G, which is deposited as DSM 32906,
*Lactobacillus paracasei* LB113R, which is deposited as DSM 32907,
*Lactobacillus plantarum* LB244R, which is deposited as DSM 32996,
*Lactobacillus paracasei* LB116R, which is deposited as DSM 32908,
*Enterococcus faecium* LB276R, which is deposited as DSM 32997,
*Lactobacillus plantarum* LB316R, which is deposited as DSM 33091,
*Leuconostoc mesenteriodes* LB341R,
*Leuconostoc mesenteriodes* LB349R, which is deposited as DSM 33093,
*Lactobacillus plantarum* LB356R, which is deposited as DSM 33094, and
*Lactobacillus plantarum* LB312R, which is deposited as DSM 33098,
and the composition decreases the transfer of a pathogenic microorganism between a surface of a first subject and a surface of a second subject, wherein the composition comprises a pH value in the range of pH 3-6.

35. The composition according to claim 34, wherein the composition is formulated into an emulsion; an oil; a gum; a paste; a powder; a talc; a lotion; a custard; a foam; a creme; a gel; an ointment; a suspension; a mist; or a liquid.

36. The composition according to claim 34, wherein the transfer of a pathogenic microorganism is decreased at least 10%.

37. The composition according to claim 34, wherein the pathogenic microorganism is a microorganism resistant to antibiotics.

38. The composition according to claim 34, wherein the at least one isolated lactic acid bacterium is present in the composition in an amount by weight of 0.001 wt % to 20 wt %.

39. The composition according to claim 1, wherein the genetic homology is at least 96% to a 16S rRNA gene of one or more of the bacterial strains selected from the group consisting of:
*Weissella viridescens* LB10G, which is deposited as DSM 32906,
*Lactobacillus paracasei* LB113R, which is deposited as DSM 32907,
*Lactobacillus plantarum* LB244R, which is deposited as DSM 32996,
*Lactobacillus paracasei* LB116R, which is deposited as DSM 32908,
*Enterococcus faecium* LB276R, which is deposited as DSM 32997,
*Lactobacillus plantarum* LB316R, which is deposited as DSM 33091,

*Leuconostoc mesenteriodes* LB349R, which is deposited as DSM 33093,

*Lactobacillus plantarum* LB356R, which is deposited as DSM 33094, and

*Lactobacillus plantarum* LB312R, which is deposited as DSM 33098.

40. The composition according to claim 1, wherein the isolated bacterial strain is selected from the group consisting of:

*Weissella viridescens* LB10G, which is deposited as DSM 32906,

*Lactobacillus paracasei* LB113R, which is deposited as DSM 32907,

*Lactobacillus plantarum* LB244R, which is deposited as DSM 32996,

*Lactobacillus paracasei* LB116R, which is deposited as DSM 32908,

*Enterococcus faecium* LB276R, which is deposited as DSM 32997,

*Lactobacillus plantarum* LB316R, which is deposited as DSM 33091

*Leuconostoc mesenteriodes* LB349R, which is deposited as DSM 33093,

*Lactobacillus plantarum* LB356R, which is deposited as DSM 33094, and

*Lactobacillus plantarum* LB312R, which is deposited as DSM 33098.

* * * * *